United States Patent
Schallek et al.

(10) Patent No.: US 10,694,944 B2
(45) Date of Patent: Jun. 30, 2020

(54) SYSTEM AND METHOD FOR ENHANCED CONTRAST IMAGING BASED ON DETECTION OF DIFFERENT PORTIONS OF A LATERAL POINT-SPREAD OF LIGHT PATTERN

(71) Applicants: Jesse Schallek, Rochester, NY (US); Raul Andres Guevara-Torres, Rochester, NY (US)

(72) Inventors: Jesse Schallek, Rochester, NY (US); Raul Andres Guevara-Torres, Rochester, NY (US)

(73) Assignee: University of Rochester, Rochester, NY (US)

( * ) Notice: Subject to any disclaimer, the term of this patent is extended or adjusted under 35 U.S.C. 154(b) by 141 days.

(21) Appl. No.: 15/563,035

(22) PCT Filed: Mar. 23, 2016

(86) PCT No.: PCT/US2016/023730
§ 371 (c)(1),
(2) Date: Sep. 29, 2017

(87) PCT Pub. No.: WO2016/160447
PCT Pub. Date: Oct. 6, 2016

(65) Prior Publication Data
US 2018/0338679 A1    Nov. 29, 2018

Related U.S. Application Data

(60) Provisional application No. 62/142,619, filed on Apr. 3, 2015.

(51) Int. Cl.
*A61B 3/14* (2006.01)
*A61B 3/10* (2006.01)
(Continued)

(52) U.S. Cl.
CPC .............. *A61B 3/145* (2013.01); *A61B 3/102* (2013.01); *A61B 3/13* (2013.01); *G06T 7/11* (2017.01)

(58) Field of Classification Search
CPC ... A61B 3/0008; A61B 3/0025; A61B 3/0041; A61B 3/0091; A61B 3/02; A61B 3/0325;
(Continued)

(56) References Cited

U.S. PATENT DOCUMENTS

2006/0203195 A1    9/2006  Squire et al.
2014/0333898 A1*  11/2014  Boate ................... A61B 3/12
                                                 351/221

FOREIGN PATENT DOCUMENTS

DE           102011102176 A1 *  11/2012  ........... A61B 3/1015

OTHER PUBLICATIONS

ISA/European Patent Office, International Search Report and Written Opinion for Corresponding International Application No. PCT/US2016/023730, dated Jun. 22, 2016 (11 pgs).
(Continued)

*Primary Examiner* — Mustak Choudhury
(74) *Attorney, Agent, or Firm* — Harris Beach PLLC

(57) ABSTRACT

An ophthalmic imaging system for imaging an axial and lateral point-spread of light distribution pattern of light reflected from a surface of an animal or human eye includes an ophthalmic imaging apparatus adapted to generate an illumination light of a surface of the eye. A detection arm includes a digital micromirror device (DMD) having an array of mirror facets. A first detector is disposed to receive a first portion of the axial and lateral point-spread of light distribution of light, and one or a plurality of additional detectors are disposed to receive a light from one or a plurality of different portions of the axial and lateral point-spread of light distribution pattern of light. A detection arm,
(Continued)

a method for imaging axial and lateral point-spread of light distribution components, and a method for auto-centering a distribution pattern in an imaging plane of a DMD device are also described.

20 Claims, 11 Drawing Sheets

(51) Int. Cl.
*A61B 3/13* (2006.01)
*G06T 7/11* (2017.01)

(58) Field of Classification Search
CPC .... A61B 3/10; A61B 3/12; A61B 3/13; A61B 3/102; A61B 3/103; A61B 3/107; A61B 3/113; A61B 3/117; A61B 3/145; A61B 3/152; A61B 3/1015; A61B 3/1225; G03B 21/008; G03B 21/14; G03B 21/20; G03B 21/147; G03B 21/204; G03B 21/2033; G03B 21/2086; G06T 7/11; G02B 27/48; G02B 27/141; G02B 27/286; G02B 27/0093; G02B 5/28; G02B 5/3016; G02B 26/0833; G06K 9/00604; G02F 1/1313; G01M 11/0257; G01B 11/002

USPC .......... 351/206, 221; 250/203.1, 206.1, 235; 600/544, 558
See application file for complete search history.

(56) References Cited

OTHER PUBLICATIONS

Geng, Ying, et al., "Adaptive Optics Retinal Imaging in the Living Mouse Eye," 2012, Biomedical Optics Express, vol. 3, No. 4, pp. 715-734.
Huang, David, et al., "Optical Coherence Tomography," 1991, Science, vol. 254, pp. 1178-1181.
Jeon, Chang-Jin, et al., "The Major Cell Populations of the Mouse Retina," 1998, The Journal of Neuroscience, vol. 18, pp. 8936-8946.
Liang, Junzhong, et al., "Supernormal Vision and High-Resolution Retinal Imaging Through Adaptive Optics," 1997, Journal of Optical Society of America A, vol. 14, pp. 2884-2892.
Williams, Robert W., et al., "Genetic Dissection of Retinal Development," 1998, Cell & Developmental Biology, vol. 9, pp. 249-255.
Zhong, Zhangyi, et al., "In Vivo Measurement of Erythrocyte Velocity and Retinal Blood Flow Using Adaptive Optics Scanning Laser Ophthalmoscopy," 2008, Optics Express, vol. 16, pp. 12746-12756.

* cited by examiner

Neutral
"0" Detector 1
"1" Detector N

|  | Horizontal Cell Density for C57BL/6J (cells/mm2) |
|---|---|
| Williams et al. | 1151+-17.5 |
| Raven and Reese | ~1500 |
| Jeon et al. (Small Population) | ~2000 |
| Lui et al | 1100 |
| Rochester | 1148+-330 |

FIG. 15

SYSTEM AND METHOD FOR ENHANCED CONTRAST IMAGING BASED ON DETECTION OF DIFFERENT PORTIONS OF A LATERAL POINT-SPREAD OF LIGHT PATTERN

CROSS-REFERENCE TO RELATED APPLICATIONS

This application is a national stage application under 35 U.S.C. § 371 of PCT Application No. PCT/US2016/023730, filed Mar. 23, 2016, IMAGING MODALITIES USING A REFLECTIVE APERTURE ARRAY IN THE IMAGING PLANE TO DYNAMICALLY IMAGE AND COMPARE COMPONENTS OF THE DIFFRACTION PATTERN AND IMAGING POINT-SPREAD FUNCTION published as WO2016160447 A1, which claims priority to and the benefit of U.S. provisional patent application Ser. No. 62/142,619, IMAGING MODALITIES USING A REFLECTIVE APERTURE ARRAY IN THE IMAGING PLANE TO DYNAMICALLY IMAGE AND COMPARE COMPONENTS OF THE DIFFRACTION PATTERN AND IMAGING POINT-SPREAD FUNCTION, filed Apr. 3, 2015, which applications are incorporated herein by reference in their entirety.

FIELD OF THE APPLICATION

The application relates to ophthalmic imaging devices and particularly to ophthalmic imaging device detection arms.

BACKGROUND

The scanning light ophthalmoscope (SLO), including the adaptive optics scanning light ophthalmoscope (AOSLO), is currently known in the art. SLO techniques of the prior art generally include a relatively fast laser based line scanner coupled with movement of the line scan typically in a transverse direction (about normal to the one dimensional (1D) line scan). Successive 1D scans advance in the transverse direction across the surface being imaged, to generate a two dimensional (2D) image of an area. The 1D line scans are typically relatively narrow. Reflected scanned light from a surface, such as in biomedical applications, is detected by a SLO detection arm.

Other ophthalmic imaging devices known in art include optical coherence tomography (OCT) apparatus, line scan camera and the flood illuminated Fundus camera.

SUMMARY

According to one aspect, an ophthalmic imaging system for imaging an axial and lateral point-spread of light distribution pattern of light reflected from a surface of an animal or human eye includes an ophthalmic imaging apparatus adapted to generate an illumination light on a surface of the animal or human eye. A detection arm is in optical communication with a reflected light caused by the illumination light of a surface of the animal or human eye to receive an axial and lateral point-spread of light distribution pattern of said reflected light. The detection arm includes a digital micromirror device (DMD) having an array of mirror facets. The detection arm also includes a first detector, and one or a plurality of additional detectors. The detection arm also includes a first detector, and one or a plurality of additional detectors. The first detector and one or a plurality of additional detectors are disposed to receive a first portion of the axial and lateral point-spread of light distribution of light as reflected by one or more mirror facets of the DMD. The one or a plurality of additional detectors are disposed to receive a light from one or a plurality of different portions of the axial and lateral point-spread of light distribution pattern of light as reflected by one or more different mirror facets of the DMD. A computer is adapted to run a DMD control process. The computer is communicatively coupled to the DMD and adapted to control a plurality of facets of the array of mirror facets so as to direct the first portion of the axial and lateral point-spread of light distribution pattern of light to the first detector and at least another portion of the axial and lateral point-spread of light distribution pattern of light to at least another detector.

In one embodiment, the DMD is disposed about in the imaging plane of the reflected light.

In another embodiment, the DMD is disposed above or below a plane of optimal focus or at multiple depth foci to provide optical contrast.

In yet another embodiment, the ophthalmic imaging apparatus includes a scanning light ophthalmoscope (SLO) or an adaptive optics scanning light ophthalmoscope (AOSLO).

In yet another embodiment, the ophthalmic imaging apparatus includes an optical coherence tomography (OCT) apparatus or a flood illuminated Fundus camera.

In yet another embodiment, at least one of the detectors includes a photomultiplier tube (PMT).

In yet another embodiment, at least one of the detectors includes an avalanche photodiode (APD).

In yet another embodiment, the first portion of the axial and lateral point-spread of light distribution pattern includes a left portion or a right portion of the lateral point-spread of light distribution pattern.

In yet another embodiment, the first portion of the axial and lateral point-spread of light distribution pattern includes a center portion or a surround portion of a center-surround axial and lateral point-spread of light distribution pattern.

In yet another embodiment, the first portion of the axial and lateral point-spread of light distribution pattern includes a part of an annular configuration axial and lateral point-spread of light distribution pattern.

In yet another embodiment, the first portion of the axial and lateral point-spread of light distribution pattern includes a part of a radial angle configuration axial and lateral point-spread of light distribution pattern.

In yet another embodiment, the first portion of the axial and lateral point-spread of light distribution pattern includes a part of a complex axial and lateral point-spread of light distribution pattern.

According to another aspect, a detection arm for imaging axial and lateral point-spread of light distribution components of a light reflected from a surface includes a digital micromirror device (DMD) having an array of a plurality of mirror facets. The DMD is adapted to be disposed to be in optical communication with and disposed in an imaging plane of an axial and lateral point-spread of light distribution pattern of a reflected light caused by a light illuminating a surface. The detection arm also includes a first detector and one or a plurality of additional detectors. The first detector is disposed to receive a first portion of the axial and lateral point-spread of light distribution pattern, and the one or a plurality of additional detectors are disposed to receive one or a plurality of different portions of the axial and lateral point-spread of light distribution pattern. The detection arm is adapted to be communicatively coupled to a computer configured to control one to N mirror facets of the DMD to reflect the first portion of the axial and lateral point-spread of light distribution pattern to the first detector and to reflect the one or a plurality of different portions of the axial and lateral point-spread of light distribution pattern to the one or a plurality of additional detectors.

According to yet another aspect, a method for imaging axial and lateral point-spread of light distribution components of light reflected from a surface of an animal or human eye includes: providing an ophthalmic imaging apparatus and a digital micromirror device (DMD) detection arm having a first detector, and one or a plurality of additional detectors; imaging the surface of an animal or human eye with the ophthalmic imaging apparatus; controlling one to N micro mirrors of the DMD to reflect a first portion of an axial and lateral point-spread of light distribution pattern to the first detector and different portions of the axial and lateral point-spread of light distribution pattern to the one or a plurality of additional detectors; receiving a light of the first portion of the axial and lateral point-spread of light distribution pattern at the first detector and receiving a light of from the one or a plurality of different portions of the axial and lateral point-spread of light distribution pattern at the one or a plurality of additional detectors; and calculating a processed image by an axial and lateral point-spread of light distribution pattern calculation technique as an ophthalmic imaging apparatus imaging light illuminates the surface of the animal or human eye based on a light measurement of the first detector and the one or a plurality of additional detectors.

In one embodiment, the step of providing an ophthalmic imaging apparatus includes providing a scanning light ophthalmoscope (SLO) or an adaptive optics scanning light ophthalmoscope (AOSLO).

In another embodiment, the step of imaging includes scanning the surface of an animal or human eye.

In yet another embodiment, the axial and lateral point-spread of light distribution pattern calculation technique includes a left-right pattern calculation technique.

In yet another embodiment, the axial and lateral point-spread of light distribution pattern calculation technique includes a center-surround pattern calculation technique.

In yet another embodiment, the axial and lateral point-spread of light distribution pattern calculation technique includes an annular configuration calculation technique.

In yet another embodiment, the axial and lateral point-spread of light distribution pattern calculation technique includes a radial angle configuration calculation technique.

In yet another embodiment, the axial and lateral point-spread of light distribution pattern calculation technique includes a complex pattern calculation technique.

According to yet another aspect, a method for auto-centering an axial and lateral point-spread of light distribution pattern in an imaging plane of a digital micromirror (DMD) device includes: providing an ophthalmic imaging apparatus to image a surface and a detection arm having a digital micromirror device (DMD) including an array of a plurality of micromirrors and at least one detector; imaging the surface with the ophthalmic imaging apparatus to cause a light to be reflected from the surface onto an imaging plane causing at least a portion of an axial and lateral point-spread of light distribution pattern on the imaging plane; controlling successively one or more micro mirrors of the plurality of micromirrors of the DMD disposed in the imaging plane to reflect light from the imaging plane to the at least one detector; processing values based on the light received by the at least one detector as the one or more micromirrors of the DMD are controlled successively to identify a center of an axial and lateral point-spread of light distribution pattern on a surface of the DMD; and setting a pattern of DMD facets to reflect a first portion of the axial and lateral point-spread of light distribution pattern to the at least one detector and one or a plurality of different portions of the axial and lateral point-spread of light distribution pattern to one or more of a plurality of additional detectors.

In one embodiment, the step of providing includes providing a scanning light ophthalmoscope (SLO) system for scanning a surface and a detection arm having a digital micromirror device (DMD) including an array of a plurality of micromirrors and at least one detector, and the step of imaging includes scanning the surface with the SLO to cause a light to be reflected from the surface onto an imaging plane causing at least a portion of an axial and lateral point-spread of light distribution pattern on the imaging plane.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 15 shows Table 1 comparing our horizontal cell density results with studies of the prior art.

DETAILED DESCRIPTION

Figure 1:
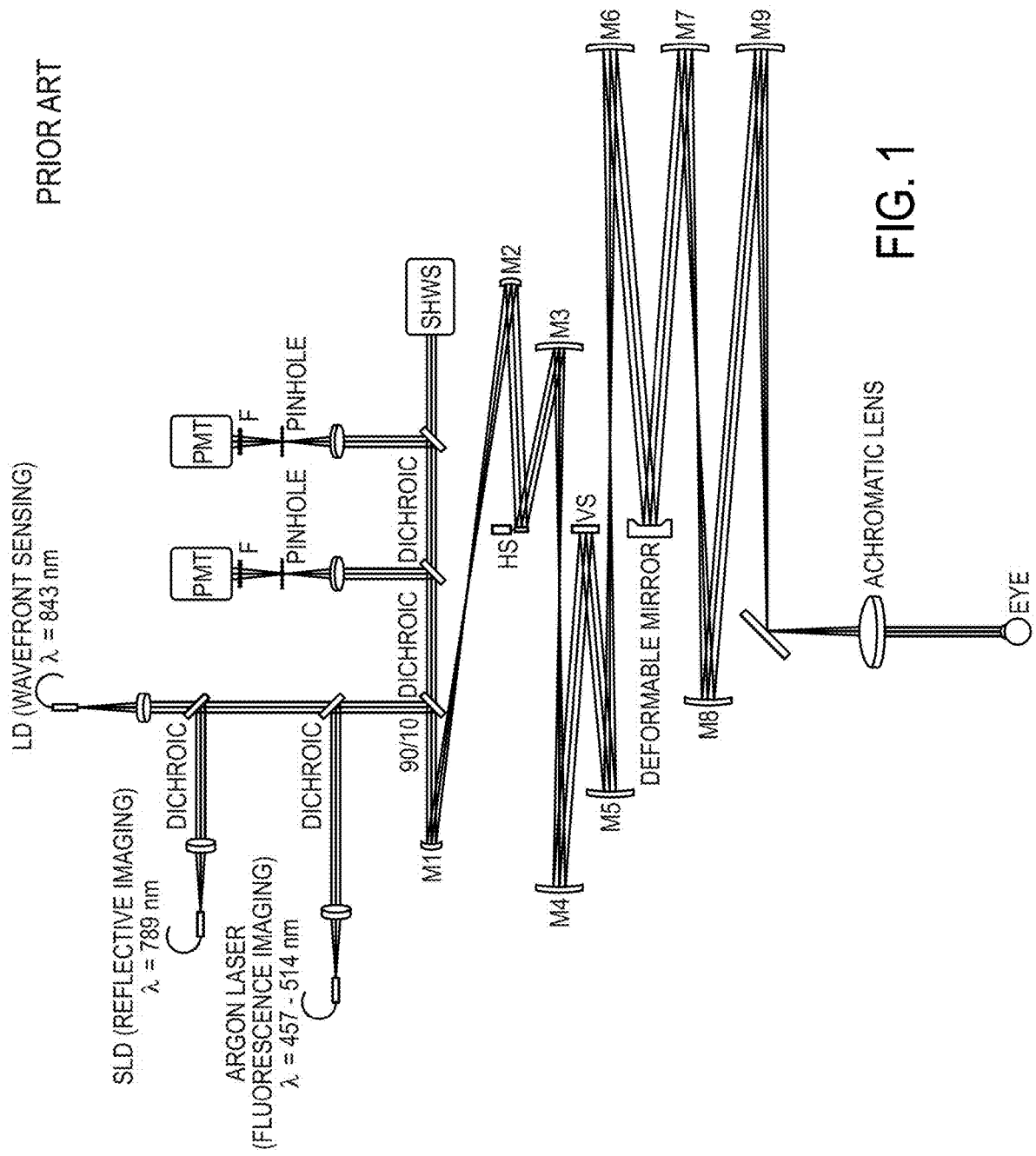
FIG. 1 shows a schematic diagram of a prior art AOSLO.

Definitions:

Detector: A detector as used herein includes any light detector suitable to receive a reflected light from a mirror. It is understood by those skilled in the art that the output of such a detector can be, for example, a current, a voltage, pulses, or a digital value. It will also be understood that a detector can include signal conditioning electronics (e.g. one or more amplifiers, filters, and/or one or more power supplies and/or bias power supplies). A detector can also include related electronic circuitry which may be wired to the light receiving or light sensitive part of the detector and may or may not be physically present in a single detector box or housing. Detectors of the new detection arm as described hereinbelow are typically photomultiplier tube (PMT) based light detectors. However, other suitable light detectors include, for example, avalanche photodiodes (APD), a charged coupled device(CCD), a complementary metal-oxide-semiconductor (CMOS) or a bolometer.

Axial and lateral point-spread of light distribution pattern: Axial and lateral point-spread of light distribution pattern includes an Airy pattern, however as distinguished from a theoretical Airy pattern alone, describes the theoretical or actual spatial distribution of light in both axial and lateral dimensions representing the diffraction or scattering pattern of light and combination of light components from a plurality of axial focus depths and lateral point-spread of light at or near the detector plane. Thus, in the new systems and methods described hereinbelow, it was realized how to use the axial and lateral point spread function which has been found to provide 3D information in the point spread information, information which was not previously available from the theoretical Airy pattern which can only provide 2D information. Also, the new systems and methods described hereinbelow including the detection with one to N detectors of the axial and lateral point spread function, provide information beyond the traditional approach that collect light from the center portion of the point spread function. Advantages over the prior art include an enhancement of the contrast from translucent objects, such as, for example, objects found in biological tissue.

In some embodiments, as opposed to at or near the detector plane, positions above and below the plane of optimal focus (or multiple depth foci) are compared such as to enhance contrast.

Axial and lateral point-spread of light distribution pattern calculation technique: An axial and lateral point-spread of light distribution pattern calculation technique as used herein splits an axial and lateral point-spread of light distribution pattern image into two or more portions at about the axial and lateral point-spread of light distribution pattern image plane. Light from the two or more portions of the axial and lateral point-spread of light distribution pattern is directed to two or more detectors. The axial and lateral point-spread of light distribution pattern can be split into portions according to a predefined pattern, such as, for example, a left-right pattern, a center-surround pattern, an annular configuration, a radial angle configuration, complex patterns, etc. The calculation can be, for example, with two detectors, a subtraction of the value (e.g. light magnitude) of one detector from another. The subtraction, division, fractional difference (or other operation) can be performed in opposite configurations (left-right, up-down, about 45 deg-225 deg or about 135 deg-315 deg). The different channels can be either an addition of each subtracted image or an addition of the subtracted images in frequency domain; with a higher weight for frequency components perpendicular to the edges and a smaller weight to frequency components parallel to the edge. For example in the case of a left-right subtraction, the components the frequencies along the x-axis will have a higher weight than the frequencies along the y-axis.

Imaging plane: Unless otherwise stated, refers to an imaging plane of light originating, or reflecting from, the retina, or other objects within the eye.

Reflected light: Unless otherwise stated, reflected light as used hereinbelow includes both light reflection from the illumination (e.g. a flood illumination or a scanned light illumination as well as any fluorescent emissions (e.g. fluorescent emissions from a surface being imaged).

While the detailed examples describe the new detection arm structures and methods with regard to a scanning light ophthalmoscope (SLO), the new detection arm structures and methods also apply to any other suitable ophthalmic imaging device, such as, for example, an optical coherence tomography (OCT), a flood illuminated fundus camera, a line-scan ophthalmoscope camera.

As described hereinabove, the scanning light ophthalmoscope (SLO), including the adaptive optics scanning light ophthalmoscope (AOSLO), is an example of a 2D imaging tool currently known in the art. SLO techniques of the prior art generally include a relatively fast laser based line scanner coupled with movement of the line scan typically in a transverse direction (about normal to the one dimensional (1D) line scan). Successive 1D scans advance in the transverse direction across the surface being imaged, to generate a two dimensional (2D) image of an area. The 1D line scans are typically relatively narrow. In the case of analog sensing, such as for example by laser light reflected back to and detected by a detector, such as for example, a photomultiplier tube (PMT), the line scan data is generally digitized typically resulting in a one pixel wide digital representation of the 1D line. Also, as is known in biomedical applications, the surface area being scanned can be a sub-surface structure, such as for example structures of the human or animal eye as scanned through one or more intermediate transparent, semitransparent, or translucent structures.

As described hereinabove, SLO apparatus, including the AOSLO, is an example of a 2D imaging tool currently known in the art. For example, the University of Rochester reported use of an AOSLO for imaging the mouse eye as described by Geng, et. al. in Adaptive optics retinal imaging in the living mouse eye, Biomedical Optics Express, April 2012/Vol. 3, No. 4, pages 715, 734. A schematic layout of the prior art Geng system is shown in FIG. 1. An exemplary AOSLO was also described in co-pending U.S. patent application Ser. No. 14/483,289, REAL-TIME OPTICAL AND DIGITAL IMAGE STABILIZATION FOR ADAPTIVE OPTICS SCANNING OPHTHALMOSCOPY, filed Sep. 11, 2014 and also assigned to the University of Rochester. The '289 application is incorporated herein by reference in its entirety for all purposes.

A confocal AOSLO uses the eye as a microscope objective to image the retina in the back of the eye. The prior art detection arm of such confocal systems has a circular aperture as a pinhole that allows a subset of photons to pass to one or more detectors. The light that does not make it through the pinhole is discarded.

We realized a new detection arm that can be used with an AOSLO apparatus. By replacing the prior art pinhole, the previously discarded light can now be used in a variety of ways to make visible otherwise transparent or weakly contrasted (e.g. transparent) structures. Such structure previously went unresolved due to lack of traditional optical contrast.

Figure 2B:
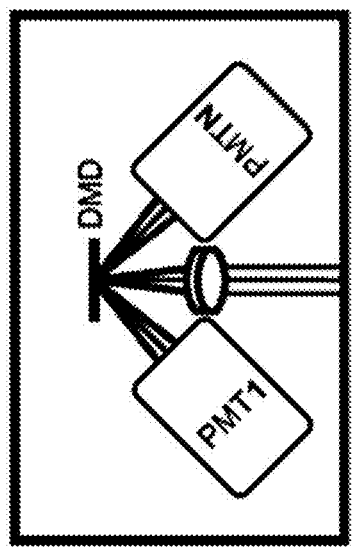
FIG. 2B shows a block diagram of the detection arm of the AOSLO of FIG. 2A, where a digital micromirror device (DMD) is placed at the imaging plane.
Figure 2A:
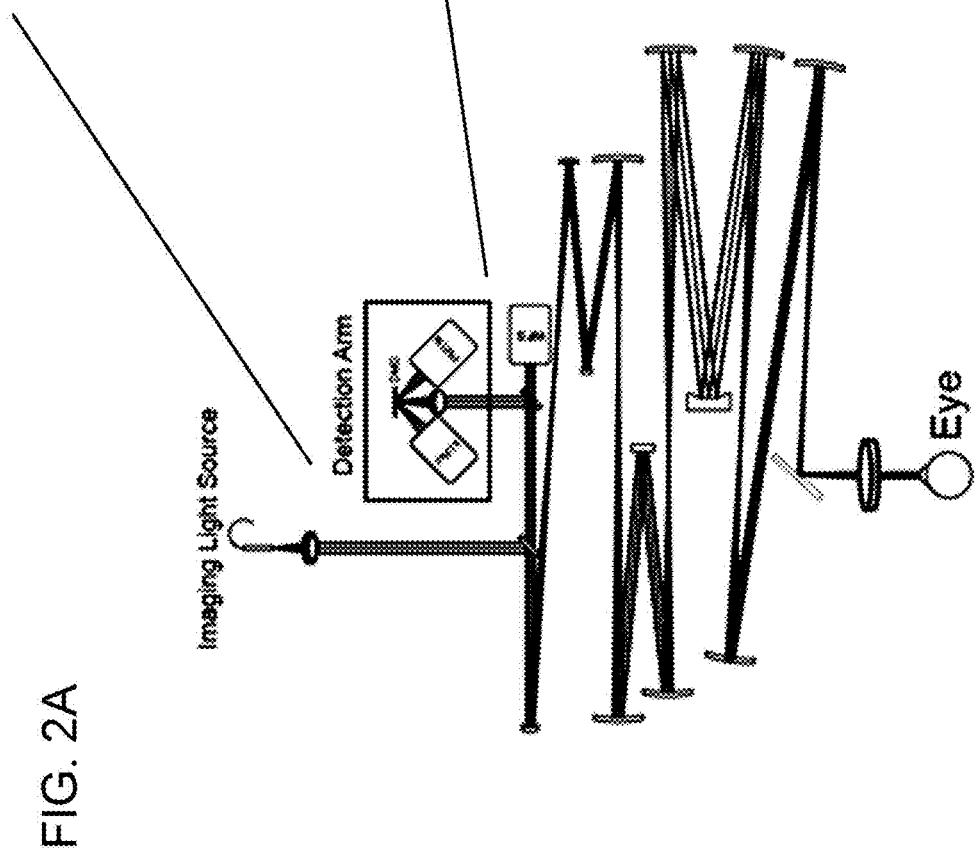
FIG. 2A shows an exemplary embodiment of the new detection arm apparatus based on the AOSLO of FIG. 1.

FIG. 2A shows an exemplary contemplated embodiment of the new detection arm installed as part of the AOSLO apparatus of FIG. 1. As shown in FIG. 2B, the pinhole of the prior art AOSLO (e.g. FIG. 1) has been replaced with a digital micromirror device (DMD) having an array of micromirrors that can be individually controlled to direct light into a variety of detectors. At the plane of a DMD disposed in an imaging plane, a single point of light is manifest as an optical axial and lateral point-spread of light distribution pattern, the spatial distribution of light as formed by diffraction (the Abbe-limit of optical resolution).

The axial and lateral point-spread of light distribution pattern can be imaged using the new AOSLO apparatus of FIG. 2A and FIG. 2B. Sample different spatial components within the axial and lateral point-spread of light distribution pattern can also be imaged to provide new previously unavailable AOSLO image contrast by mathematical or optical subtraction (or other operators such as, addition, division, normalization etc) of various axial and lateral point-spread of light distribution components.

Note that the DMD could also be placed at positions above and below the plane of optimal focus (or multiple depth foci) to provide optical contrast by comparing above and below plane information in the same way left-right information is compared to provide contrast. Whereas above, "comparing" may also refer to mathematical operations such as subtraction, division, normalization, multiplication etc)

Figure 3B:
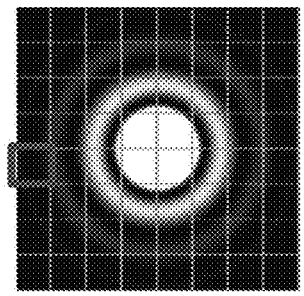
FIG. 3B shows an exemplary axial and lateral point-spread of light distribution pattern over the 2D surface of the individual micromirror facets of a DMD device.
Figure 3A:
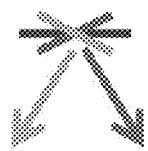
FIG. 3A shows a diagram of an exemplary DMD detection arm having 1 to N detectors.
Figure 3A:
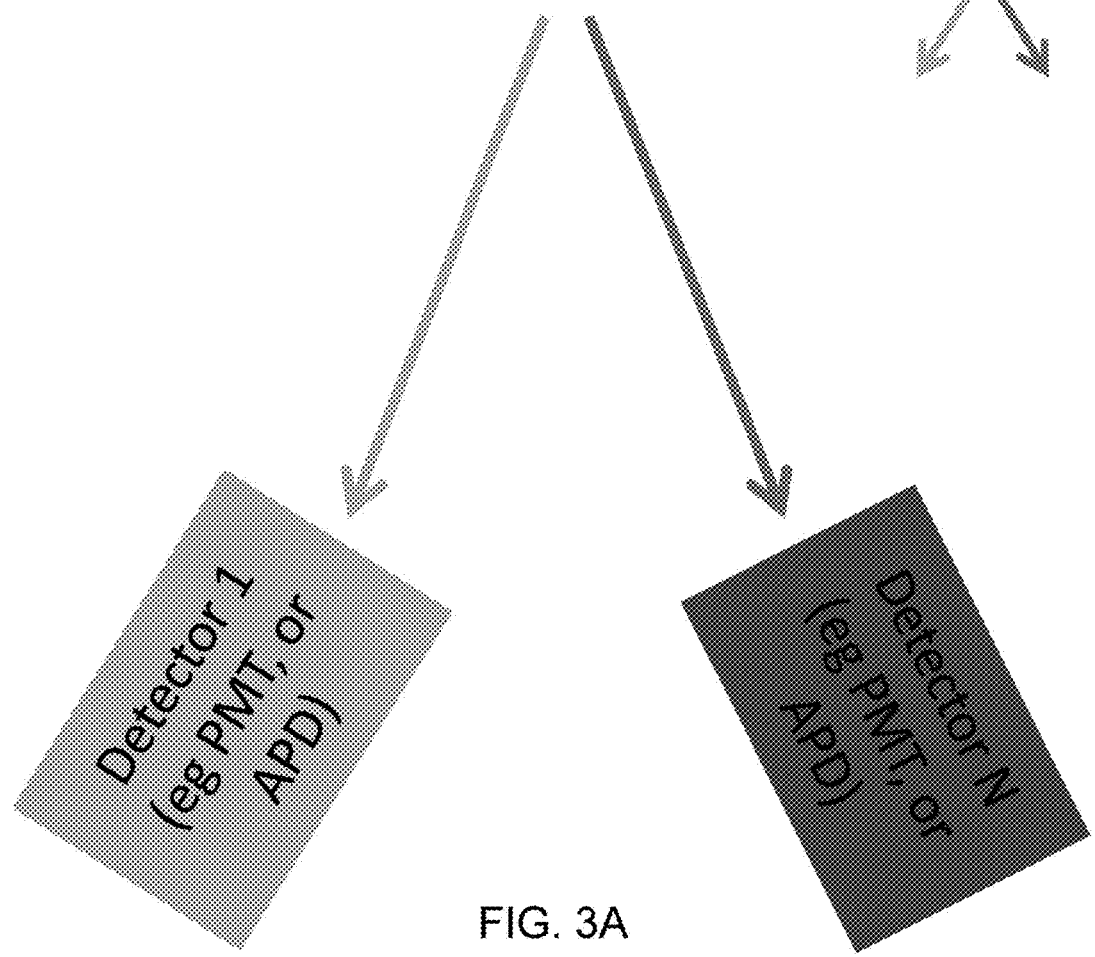

FIG. 3A shows a diagram of an exemplary DMD detection arm having 1 to N detectors. Any suitable detectors can be used, such as, for example, photomultiplier tubes (PMT) or avalanche photodiodes (APD).

FIG. 3B shows an exemplary axial and lateral pointspread of light distribution pattern over the 2D surface of the individual micromirror facets of a DMD device. Each facet can be in a neutral position (not directing light to a particular detector), directing light to detector 1, or directing light to another detector (e.g. detector 2 to detector N). The examples which follow show two detectors for simplicity in introducing various exemplary facet configurations. However, it is understood that there can be any suitable number of detectors, two to N detectors.

Figure 4A:
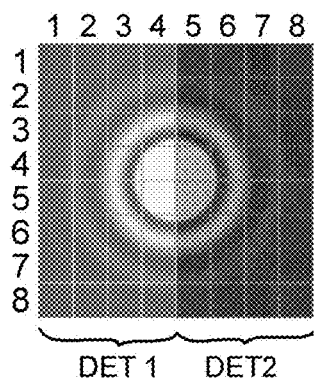
FIG. 4A shows an illustration of an exemplary left-right technique.

FIG. 4A shows an illustration of an axial and lateral point-spread of light distribution pattern image centered on a DMD array, such as the DMD array of FIG. 3A. The exemplary 64 DMD array facets are numbered for convenience, columns 1 to 8, and rows 1 to 8. Any suitable number of facets can be used.

A particular facet can be referenced by (column, row, such as for example, facet (4, 4) which in the exemplary illustration of FIG. 4A falls slightly above and left of center in the axial and lateral point-spread of light distribution disk.

As described hereinabove, we believe that the axial and lateral point-spread of light distribution components be used in a variety of ways to make visible in images, transparent or weakly contrasted (e.g. transparent) structures that were previously unresolved due to lack of traditional optical contrast. For example, in FIG. 4A, in a left-right calculation, light from the facets of the left side of the DMD array (columns 1 to 4) is directed towards a first detector (DET 1). Light from the facets of the right side of the DMD array (columns 1 to 4) is directed towards a second detector (DET 2).

Figure 4B:
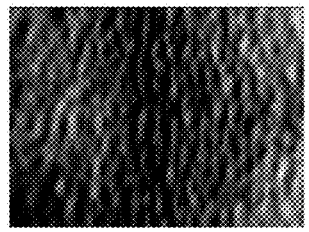
FIG. 4B shows an image of exemplary retinal cell somas simulating the left-right technique of FIG. 4A by DMD, using a knife edge prism in a proof of concept AOSLO implementation.
Figure 4C:
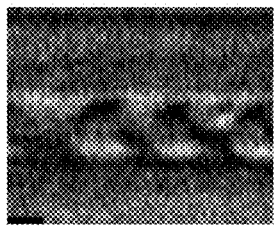
FIG. 4C shows an actual image of exemplary blood cells in the retina simulating the left-right technique of FIG. 4A by DMD, using a knife edge in a proof of concept AOSLO implementation.

As described in more detail hereinbelow in more detail, in a proof of concept configuration we used an optical knife edge in place of the prior art pinhole in a detection arm of the University of Rochester AOSLO. The knife edge splits the light beam into 2 PMTs, just like a DMD would in a static Left-Right configuration (or top half-bottom half configuration). The images of retinal cell somas (FIG. 4B) and moving blood cells (FIG. 4C) are actual proof of concept images realized in our AOSLO instrument using the proof of concept knife-edge beam diversion apparatus.

Figure 5:
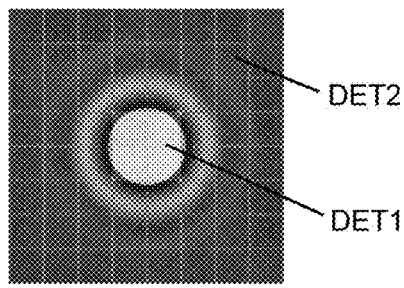
FIG. 5 shows an illustration of an exemplary center-surround axial and lateral point-spread of light distribution pattern technique.

Other axial and lateral point-spread of light distribution pattern calculations are contemplated. For example, FIG. 5 shows a center-surround axial and lateral point-spread of light distribution pattern calculation. In the center-surround axial and lateral point-spread of light distribution pattern calculation, facets reflecting light from the axial and lateral point-spread of light distribution disk are reflected to DET 1, while facets reflecting light from the surrounding axial and lateral point-spread of light distribution pattern, including the Airy rings are reflected to another detector (e.g. DET 2).

Figure 6:
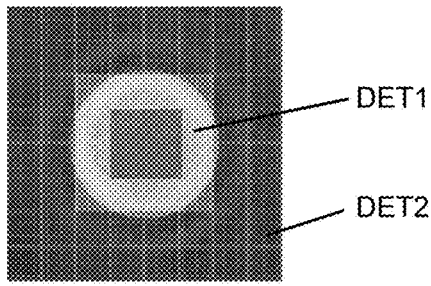
FIG. 6 shows an illustration of an exemplary annular configuration technique.

FIG. 6 shows an annular configuration technique where light of the first Airy ring is directed towards a first detector (e.g. DET 1) and some or all of the light of the axial and lateral point-spread of light distribution pattern from other facets is directed towards another detector (e.g. DET 2).

Figure 7:
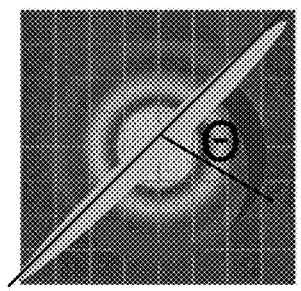
FIG. 7 shows an illustration of an exemplary radial angle technique.

FIG. 7 shows a radial angle configuration where light of the axial and lateral point-spread of light distribution pattern from a line about one or two facets wide across the axial and lateral point-spread of light distribution pattern can be directed to a first detector (e.g. DET 1), while some or all of the remaining light of the axial and lateral point-spread of light distribution pattern can be directed by other facets to another detector (e.g. DET 2).

Figure 8:
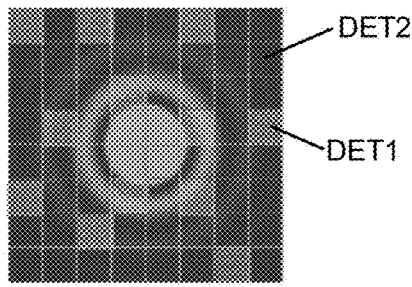
FIG. 8 shows an illustration of an exemplary complex pattern technique.

FIG. 8 shows a complex pattern technique where in more of a "checker board" pattern, light from various facets across the axial and lateral point-spread of light distribution Pattern can be directed towards a first detector (e.g. DET 1), while some or all of the remaining axial and lateral point-spread of light distribution pattern light can be directed by other DMD facets to a second detector (e.g. DET 2).

While the exemplary DMD configurations of FIG. 4A to FIG. 8 are illustrated for simplicity with only two detectors, there can be any suitable number of detectors, where facets typically under computer control, are directed at predetermined detectors to satisfy any suitable desired configuration for any suitable axial and lateral point-spread of light distribution pattern calculation technique (axial and lateral point-spread of light distribution pattern calculation process).

In the simplest embodiments, such as for example, where there are two detectors, a magnitude value measured by the first detector can be subtracted from the magnitude value measured by the second detector, or vice versa. However, any suitable calculation including, for example offset or scale values for each detector can used.

Automatic Pinhole Alignment: In regular confocal microscopes precise mechanical stages are required to control the position of the pinhole. This mechanical constraint makes rapid alignment slow and prone to mechanical error.

It is contemplated that using the DMD detection arm as described hereinabove, that the new DMD detection arm apparatus will allow rapid and precise alignment of an "artificial" pinhole. The artificial pinhole is defined by the facets of the DMD which are directed into one or more detectors. For example, it is contemplated that the center-surround configuration (FIG. 5) would allow a mechanical pinhole to be simulated or emulated by diverting light from just the center of the axial and lateral point-spread of light distribution pattern to detector 1 while rejecting light from the surround. This would mimic the traditional embodiment of a mechanical pinhole found in prior art confocal microscopes and AOSLOs.

The state of the DMD can also be changed to effectively tune the size of virtual pinhole (i.e. positional state of DMD facets, without an actual pinhole) by process software running on a computer to perform rapid and automated artificial pinhole alignment. For example, automatic DMD alignment is contemplated by use of a search algorithm process that identifies the optimal position of the equivalent "pinhole" by selectively turning DMD micromirrors on and off in response to light measured by one or more detectors. Such search algorithms for imaging and optical alignment are well known. One contemplated process algorithm can individually activate one micromirror at a time to create a 2-dimensional array of the light distribution at the plane of the DMD. The position of the micromirror that reflects the largest amount of light will correspond to the center of the imaging point-spread function, and the logical place to position the artificial pinhole for confocal imaging approaches.

Figure 9:
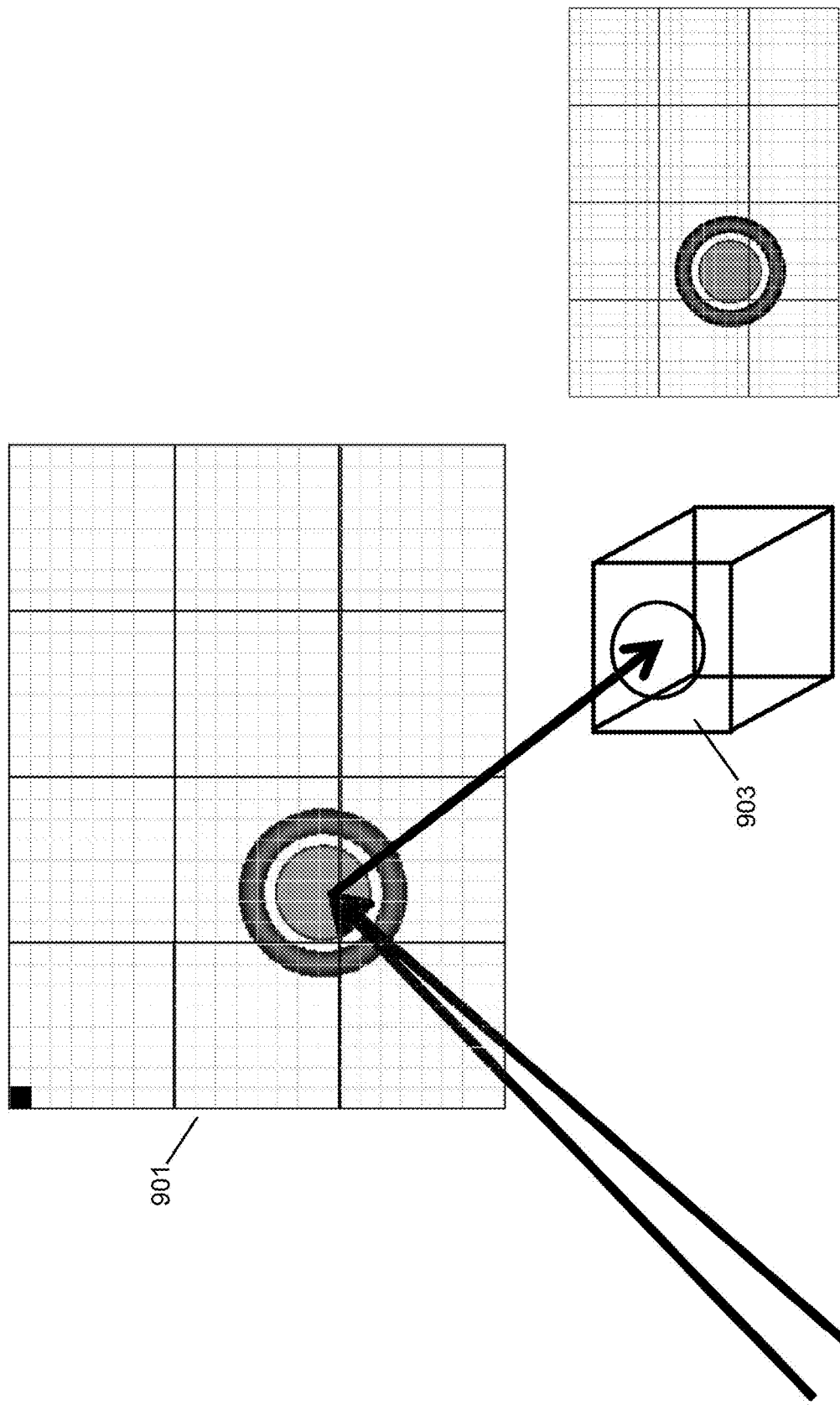
FIG. 9 is an illustration showing detection of an axial and lateral point-spread of light distribution disk in the lower left of a DMD array.
Figure 10:
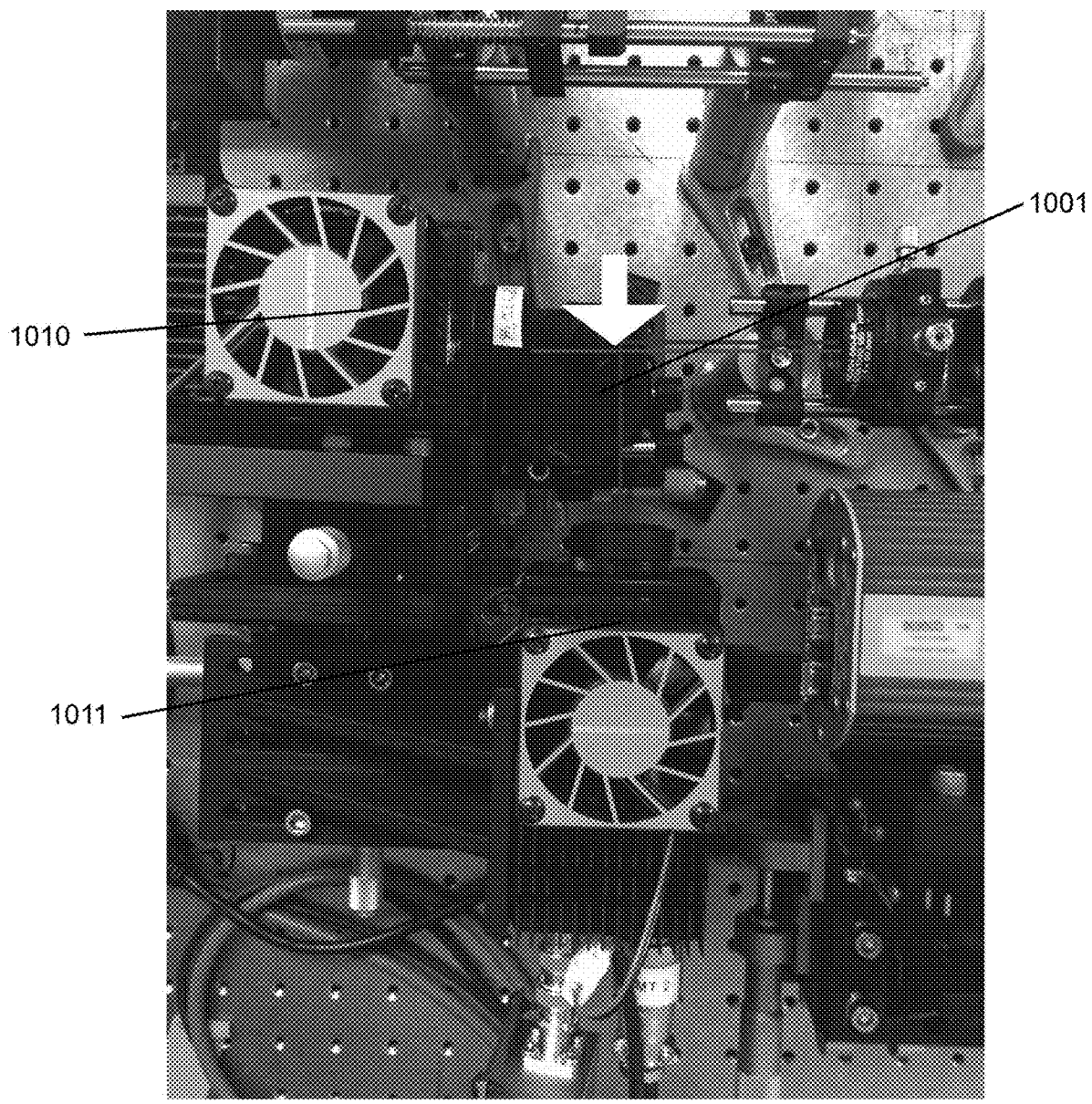
FIG. 10 shows an illustration of an exemplary detection arm of an AOSLO.

For example, FIG. 9 shows detection of an axial and lateral point-spread of light distribution disk in the lower left of a DMD array 901 by a detector 903. By selectively turning DMD array 901 micromirrors on and off a search process running on a computer can identify which facet or facets define the center or location of the axial and lateral point-spread of light distribution pattern on DMD array 901. As long as the desired parts of the axial and lateral point-spread of light distribution pattern are somewhere on the surface of the DMD array 901, no other optical components need to be adjusted to continue imaging of a specimen (e.g. in vivo imaging of the retina of an animal or human eye).

example: FIG. 10 shows an illustration of one exemplary detection arm of an AOSLO. Exemplary PMT detectors 1010 and 1011 are shown receiving light from a device marked by the arrow. It is contemplated that the DMD device can replace the prior art mirror device 1001 shown in FIG. 10 to provide the new DMD based detection arm described hereinabove.

example: One exemplary suitable AOSLO apparatus includes the University of Rochester Adaptive Optics Scanning Light Ophthalmoscope (AOSLO) discussed hereinabove and shown in FIG. 1. This AOSLO includes five, 4f telescope pairs that successively relay the eye's pupil into the deformable mirror and the horizontal and vertical scanners. It uses an 850 nm laser from Qphoonics (Ann Arbor, Mich.) as a wavefront sensor. It has a 796 nm superluminescent diode (Superlum, Carrigtwohill, Ireland) as a light source. A deformable mirror provided aberration correction and defocus control (ALPAO, Montbonnot-Saint-Martin, France). The fast scanner operates in the horizontal direction at a rate of about 15 kHz and the vertical scanner at a rate of about 25 Hz where data is acquired by a Matrox Odyssey data acquisition board (Matrox International Corporation, Quebec, Canada).

The detection arm of the exemplary prior art AOSLO (FIG. 1) includes a collimating lens that focuses light into a pinhole which allows the passage of a subset of photons that are further collected by a photomultiplier tube (PMT).

example: Suitable detectors that can also be used in the new detection arm, include, for example, the near infrared DLP DLP4500NIR, available from Texas Instruments of Dallas, Tex., or the Hamamatsu Photomultiplier tube H7422-50 available from Hamamatsu City, Japan.

example: As described hereinabove with respect to FIG. 4A and FIG. 4B, proof of concept tests of the contemplated DMD based detection arm described hereinabove were implemented on the University of Rochester AOSLO using a knife edge device. For the proof of concept studies for the contemplated DMD based detection arm, the UR AOSLO detection arm was modified by introducing a silver coated knife edge (available from THORLABS of Newton, N.J.), to separate the right and left information at the retinal plane where pinhole was previously located. Half of the light passed along the optical axis of the focusing lens and was further detected by PMT1, while the second half was reflected by the knife edge and directed towards a second PMT2. Capture of the two simultaneous channels was performed without reimaging optics. While a registration channel was not simultaneously captured, we used a registration strategy based on only split detection information.

The proof of concept images are actual images of in vivo mouse eyes. The animal study procedures were approved by the University Committee on Animal Resources and followed the guidelines of the ARVO Statement for the Use of Animals in Ophthalmic and Visual Research. The mouse was located in a stereotactic stage with bite bar on top of a XYZ translational stage that allowed positioning the eye's pupil at a plane conjugate to pupil of the system, while the tip and tilt allowed the navigation to a particular retinal location. The mouse pupils were dilated using an eye drop of 1% tropicamide and 2% phenylephrine(Alcon). Mice were anesthetized with an intraperitoneal injection of ket-amine/xylazine (100 mg/kg ketamine, 10 mg/kg xylazine) or with 1% insofluorane anesthesia.

Line-Scan Imaging of Blood Flow: The mouse AOSLO scanning system was designed to scan in the x and y direction to generate images at a rate of 25 Hz. Similar to (Thong et al. 2008), one application was to study the blood flow where the frame rate was increased by restricting the scanner to move only in the x direction at a rate of about 15.4 KHz. When imaging vessels perpendicular to the scan direction this allowed to capture blood cell information as they flowed through the vessel.

Image Registration: As a registration signal was not simultaneously captured in this setup, we relied on the split detection data to generate one. The first step included desinusoiding the registered sequence a using sinc interpolation algorithm, then the PMT1 value was subtracted from the value of PMT2, which generated an enhancement in the contrast. The displacements of the sequence relative to a reference frame were calculated using the maxima of the cross correlation. Once the displacements were calculated the raw data was registered applying a compensation for the displacements previously calculated. Finally the final image was calculated by averaging the registered sequence of each channel and then calculating the difference between channel 1 and channel 2.

Results

Figure 11A:
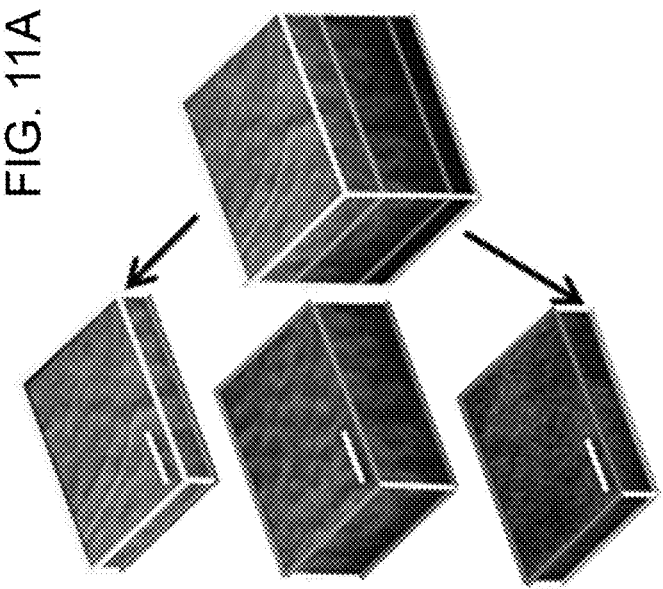
FIG. 11A shows three exemplary retinal layers.
Figure 11B:
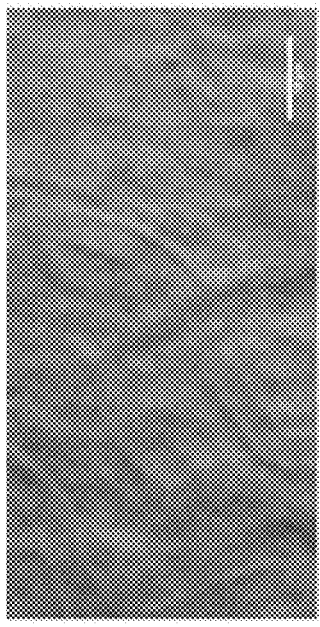
FIG. 11B shows an exemplary image of a deepest layer of vasculature.
Figure 11C:
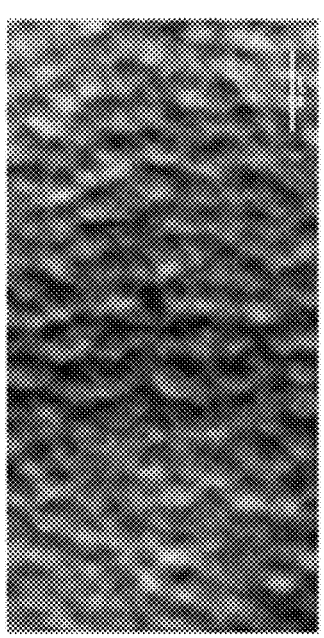
FIG. 11C shows an exemplary image of through focusing deep in the photoreceptor somas layer.
Figure 11D:
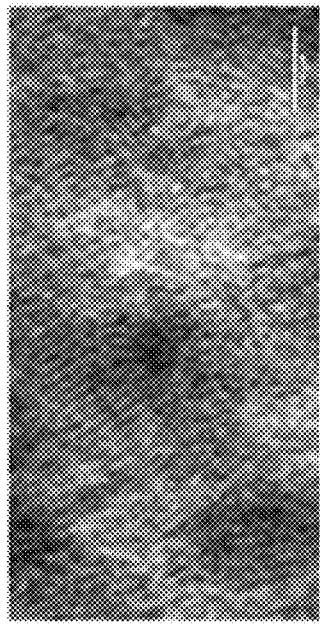
FIG. 11D shows an exemplary image of the distal photoreceptor processes.

Photoreceptor Imaging: Through focus imaging was performed between the limits of the photoreceptor area. As shown in FIG. 11A, three layers were imaged from a deepest layer of vasculature (FIG. 11B), through focusing deep in the photoreceptor somas layer (FIG. 11C), and to the distal photoreceptor processes (FIG. 11D). These exemplary proof of concept images were obtained with split detection.

Figure 12:
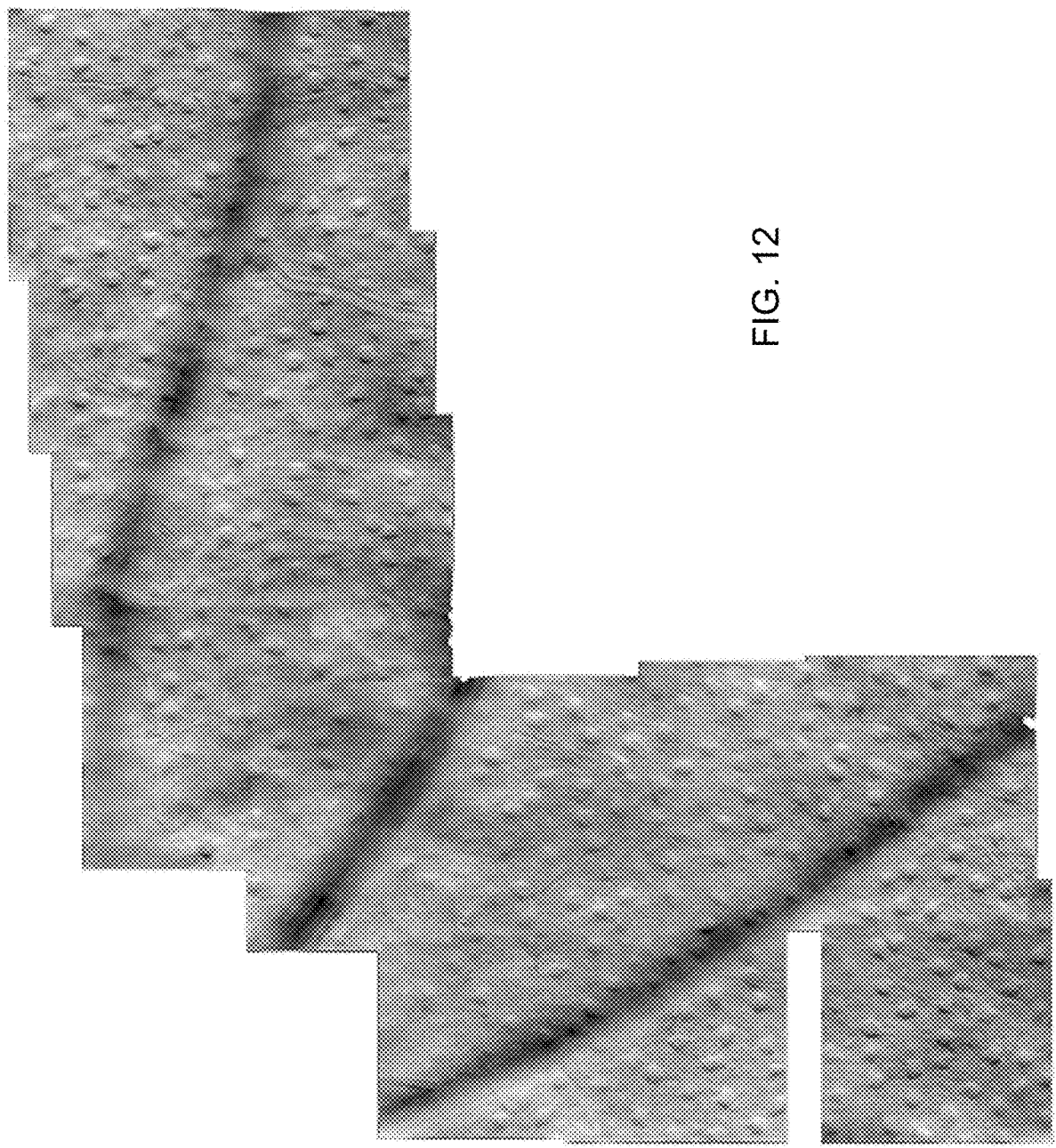
FIG. 12 shows exemplary shallower imaging from the photoreceptor cell somas.

Horizontal Cells: When imaging shallower from the photoreceptor cell somas, we were able to a sparse cell structure shown in the image of FIG. 12. Manually segmenting the densities we found a density of cells consistent with previous cell counts by previous studies using other techniques of horizontal cells in the living retina.

Figure 13:
FIG. 13 shows an exemplary high resolution erythrocyte Image acquired with the knife edge proof of concept apparatus.

FIG. 13 show an exemplary high resolution erythrocyte Image acquired with the proof of concept apparatus.

Figure 14:
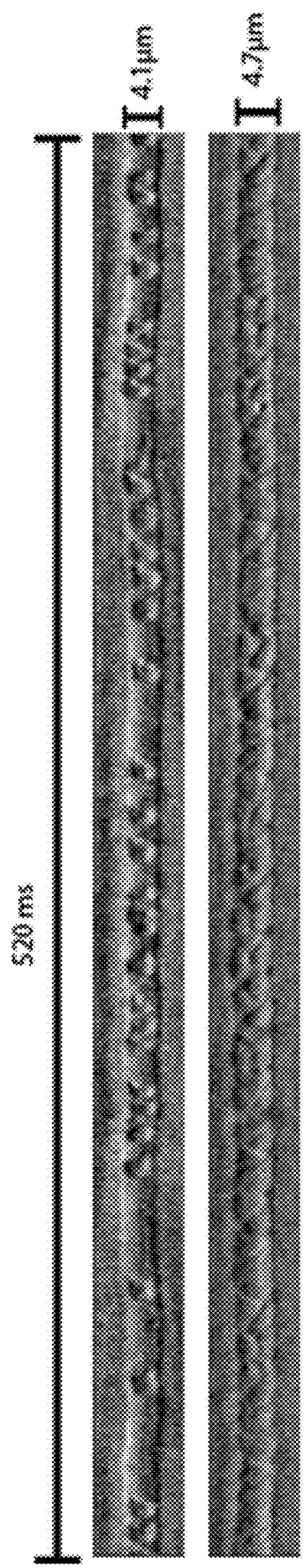
FIG. 14 shows an exemplary line scan images of blood cells as they passed through the vessel.

Line Scan Imaging of Blood Flow: Split detection allows for distinguishing individual blood cells as they pass through the vasculature. Line scan retinal imaging was also performed, which allowed us to detect the passage of blood cells as they flow through the vasculature, in a subset of capillaries, this technique allowed us to indistinguishably count each blood cell as they passed through the vessel as it can be seen in the line scan image of FIG. 14. In sparse conditions we are able to detect 80 cells per mm$^2$. Techniques of AOSLO line scan imaging were described in detail in U.S. Patent Application No. 61/933,102, SYSTEM AND METHOD FOR OBSERVING AN OBJECT IN A BLOOD VESSEL, filed Jan. 29, 2014 and also assigned to the University of Rochester. The '102 application is incorporated herein by reference in its entirety for all purposes. The increase in numerical aperture of the mouse eye helps as to detect these cells. While the photoreceptors are smaller to match with the diffraction limit, horizontal cells are close to being the same size in both humans and mice Contrast of Split Detection: The exemplary images discussed hereinabove were captured by subtraction of the right-left axial and lateral point-spread of light distribution components at the confocal plane. If the amount of light at the right and at the left of the PMT is the same then both contribution cancel out. However, when the light distribution at the confocal plane has a bias to a direction orthogonal to the knife edge, then the subtraction of the two channels acquires a signed value.

The retina is a complex multilayered tissue with a great variety of structures that create reflectance, scattering and refractive index variations, of which all play a combined role in the interactions of light in the retina. However, despite the complex multilayered tissue, a relatively simple purely reflective model of the retinal creates asymmetries at the confocal plane.

The illumination in our setup with a circular pupil creates a circularly symmetric pattern at the retina. When this light distribution interacts with a circularly symmetric object, the light distribution at the confocal plane becomes symmetric and the subtraction equals to zero. However, when the reflectance of the object is asymmetric, as in the case of an edge, this creates an asymmetric pattern at the confocal plane, and when the images are subtracted the output will be nonzero. The sign of the difference depends on whether the edge is to the right or to the left of the object.

Photoreceptor Cell Imaging: At the bottom of the photoreceptor layer we were able to image the image a cell class whose density matches with the expected number of rods in the mouse retina (e.g. by Jeon, Strettoi, and Masland 1998 using other techniques). In these images we were looking at the photoreceptor distal processes which are the combination of inner segments and outer segments. It is unlikely that we are looking at a different cell classes, as rods constitute the cell class with a largest population in the mouse retina and the cell densities of any other cell differ by at least an order of magnitude.

The deepest layer of vasculature is located in between the inner nuclear layer and the photoreceptor layer. When imaging through the photoreceptor somas, in between the photoreceptor distal processes and the deepest layer of vasculature, we are able to image a multilayered cell structure which we identify as layer of cell somas. The size of the cell somas that we captured was found to be consistent with the cell sizes found by previous studies using other techniques.

This technology is important to study and monitor the state of the photoreceptor images over time. Being able to image the same mice over time this will reduce the number of animals that need to be sacrificed to perform a given study.

Horizontal Retinal Cell Imaging: To our knowledge this is the first time that inner retinal cells have been seen in the living eye without any contrast agents. This proof of concept implementation serves as a baseline to extend these studies to image other cell classes, such as, for example, in the inner nuclear layer and in the ganglion cell layer.

Using other methods, horizontal cell density has been shown to be strongly dependent on the strain of mice, and exhibits a twofold variation between the C57BL/6 and the A/J mice (Williams et al. 1998). We measured a cell density of 9770 cells per mm$^2$ in an area of 0.28 mm$^2$. FIG. 15 shows Table 1 comparing our ("Rochester") horizontal cell density results with Williams and other studies which used apparatus of the prior art.

Line Scan Imaging of Blood Flow: The vasculature in the retina has the mayor role of delivering the required inputs to satisfy the metabolic demand and as well as to take away all the waste products that are produced here. Red blood cells are the basic units of transport of these metabolic components. Adaptive optics combined with split detection has the potential to count the passage of the smallest units of oxygen delivery.

REFERENCES

Geng, Ying, Alfredo Dubra, Lu Yin, William H. Merigan, Robin Sharma, Richard T. Libby, and David R. Williams. 2012. "Adaptive Optics Retinal Imaging in the Living Mouse Eye." Biomedical Optics Express 3 (4): 715-34. doi:10.1364/BOE.3.000715.

Huang, D., E. A. Swanson, C. P. Lin, J. S. Schuman, W. G. Stinson, W. Chang, M. R. Hee, et al. 1991. "Optical Coherence Tomography." Science 254 (5035): 1178-81. doi:10.1126/science.1957169.

Jeon, Chang-Jin, Enrica Strettoi, and Richard H. Masland. 1998. "The Major Cell Populations of the Mouse Retina." The Journal of Neuroscience 18 (21): 8936-46.

Liang, Junzhong, David R. Williams, and Donald T. Miller. 1997. "Supernormal Vision and High-Resolution Retinal Imaging through Adaptive Optics." Journal of the Optical Society of America A 14 (11): 2884-92. doi:10.1364/JOSAA.14.002884.

Williams, Robert W., Richelle C. Strom, Guomin Zhou, and Zhen Yan. 1998. "Genetic Dissection of Retinal Development." Seminars in Cell & Developmental Biology 9 (3): 249-55. doi:10.1006/scdb.1998.0236.

Zhong, Zhangyi, Benno L. Petrig, Xiaofeng Qi, and Stephen A. Burns. 2008. "In Vivo Measurement of Erythrocyte Velocity and Retinal Blood Flow Using Adaptive Optics Scanning Laser Ophthalmoscopy." Optics Express 16 (17): 12746-56. doi:10.1364/OE.16.012746.

Computer software and/or firmware used to control the new DMD based detection arm as well as other functions of a SLO, such as, for example, an AOSLO can be supplied on a computer readable non-transitory storage medium. A computer readable non-transitory storage medium as non-transitory data storage includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. An ophthalmic imaging system for imaging an axial and lateral point-spread of light distribution pattern of light reflected from a surface of an animal or human eye comprising:
    an ophthalmic imaging apparatus comprising a scanning light ophthalmoscope, or an optical coherence tomography apparatus illuminates a surface of the animal or human eye;
    a detection arm in optical communication with a reflected light caused by said illumination light on a surface of said animal or human eye to receive an axial and lateral point-spread of light distribution pattern of said reflected light comprising:
        a digital micromirror device (DMD) having an array of mirror facets;
        a first detector, and one or a plurality of additional detectors, said first detector disposed to receive a first portion of said axial and lateral point-spread of light distribution of light as reflected by one or more mirror facets of said DMD, and said one or a plurality of additional detectors disposed to receive a light from one or a plurality of different portions of said axial and lateral point-spread of light distribution pattern of light as reflected by one or more different mirror facets of said DMD; and
        a computer adapted to run a DMD control process, said computer communicatively coupled to said DMD and adapted to control a plurality of facets of said array of mirror facets so as to direct said first portion of said axial and lateral point-spread of light distribution pattern of light to said first detector and at least another portion of said axial and lateral point-spread of light distribution pattern of light to at least another detector,
        an axial and lateral point-spread of light distribution pattern calculation process to generate an enhanced contrast image of said surface of said animal or human eye based on information from said first detector and said at least another detector.

2. The ophthalmic imaging system of claim 1, wherein said DMD is disposed about in said imaging plane of said reflected light.

3. The ophthalmic imaging system of claim 1, wherein said DMD is disposed above or below a plane of optimal focus or at multiple depth foci to provide optical contrast.

4. The ophthalmic imaging system of claim 1, wherein at least one of said detectors comprises a photomultiplier tube (PMT).

5. The ophthalmic imaging system of claim 1, wherein at least one of said detectors comprises an avalanche photodiode (APD).

6. The ophthalmic imaging system of claim 1, wherein said first portion of said axial and lateral point-spread of light distribution pattern comprises a left portion or a right portion of said lateral point-spread of light distribution pattern.

7. The ophthalmic imaging system of claim 1, wherein said first portion of said axial and lateral point-spread of light distribution pattern comprises a center portion or a surround portion of a center-surround axial and lateral point-spread of light distribution pattern.

8. The ophthalmic imaging system of claim 1, wherein said first portion of said axial and lateral point-spread of light distribution pattern comprises a part of an annular configuration axial and lateral point-spread of light distribution pattern.

9. The ophthalmic imaging system of claim 1, wherein said first portion of said axial and lateral point-spread of light distribution pattern comprises a part of a radial angle configuration axial and lateral point-spread of light distribution pattern.

10. The ophthalmic imaging system of claim 1, wherein said first portion of said axial and lateral point-spread of light distribution pattern comprises a part of a complex axial and lateral point-spread of light distribution pattern.

11. A detection arm for imaging axial and lateral point-spread of light distribution components of a light reflected from a surface comprising:
    a digital micromirror device (DMD) having an array of a plurality of mirror facets, said DMD adapted to be disposed to be in optical communication with and disposed in an imaging plane of an axial and lateral point-spread of light distribution pattern of a reflected light caused by a light illuminating a surface;
    a first detector and one or a plurality of additional detectors, said first detector disposed to receive a first portion of said axial and lateral point-spread of light distribution pattern, and said one or a plurality of additional detectors disposed to receive one or a plurality of different portions of said axial and lateral point-spread of light distribution pattern;
    wherein said detection arm is adapted to be communicatively coupled to a computer configured to control one to N mirror facets of said DMD to reflect said first portion of said axial and lateral point-spread of light distribution pattern to said first detector and to reflect said one or a plurality of different portions of said axial and lateral point-spread of light distribution pattern to said one or a plurality of additional detectors, and wherein an axial and lateral point-spread of light distribution pattern calculation process generates an enhanced contrast image of said surface based on information from said first detector and said at least another detector.

12. A method for imaging axial and lateral point-spread of light distribution components of light reflected from a surface of an animal or human eye comprising:
    providing an ophthalmic imaging apparatus comprising a scanning light ophthalmoscope (SLO) or an adaptive optics scanning light ophthalmoscope (AOSLO), and a digital micromirror device (DMD) detection arm having a first detector, and one or a plurality of additional detectors;

imaging said surface of an animal or human eye with said ophthalmic imaging apparatus;

controlling one to N micro mirrors of said DMD to reflect a first portion of an axial and lateral point-spread of light distribution pattern to said first detector and different portions of said axial and lateral point-spread of light distribution pattern to said one or a plurality of additional detectors;

receiving a light of said first portion of said axial and lateral point-spread of light distribution pattern at said first detector and receiving a light of from said one or a plurality of different portions of said axial and lateral point-spread of light distribution pattern at said one or a plurality of additional detectors; and calculating a processed image by an axial and lateral point-spread of light distribution pattern calculation process to generate an enhanced contrast image of said surface of said animal or human eye based on information from said first detector and said at least another detector.

13. The method for imaging of claim 12, wherein said step of imaging said surface of an animal or human eye comprises scanning said surface of an animal or human eye.

14. The method for imaging of claim 12, wherein said axial and lateral point-spread of light distribution pattern calculation process comprises a left-right pattern calculation technique.

15. The method for imaging of claim 12, wherein said axial and lateral point-spread of light distribution pattern calculation process comprises a center-surround pattern calculation technique.

16. The method for imaging of claim 12, wherein said axial and lateral point-spread of light distribution pattern calculation process comprises an annular configuration calculation technique.

17. The method for imaging of claim 12, wherein said axial and lateral point-spread of light distribution pattern calculation process comprises a radial angle configuration calculation technique.

18. The method for imaging of claim 12, wherein said axial and lateral point-spread of light distribution pattern calculation process comprises a complex pattern calculation technique.

19. A method for auto-centering an axial and lateral point-spread of light distribution pattern in an imaging plane of a digital micromirror (DMD) device comprising:

providing a scanning light ophthalmoscope (SLO) system for scanning a surface and a detection arm having a digital micromirror device (DMD) comprising an array of a plurality of micromirrors and at least one detector and at least one additional detector;

imaging said surface with said ophthalmic imaging apparatus to cause a light to be reflected from said surface onto an imaging plane causing at least a portion of an axial and lateral point-spread of light distribution pattern on said imaging plane;

controlling successively one or more micro mirrors of said plurality of micromirrors of said DMD disposed in said imaging plane to reflect light from said imaging plane to said at least one detector;

processing values based on said light received by said at least one detector as said one or more micromirrors of said DMD are controlled successively to identify a center of an axial and lateral point-spread of light distribution pattern on a surface of said DMD;

setting a pattern of DMD facets to reflect a first portion of said axial and lateral point-spread of light distribution pattern to said at least one detector and one or a plurality of different portions of said axial and lateral point-spread of light distribution pattern to said at least one additional detector; and wherein an axial and lateral point-spread of light distribution pattern calculation process generates an enhanced contrast image of said surface based on information from said first detector and said at least another detector.

20. The method for auto-centering of claim 19, wherein said step of imaging said surface with said ophthalmic imaging apparatus comprises scanning said surface with said SLO to cause a light to be reflected from said surface onto an imaging plane causing at least a portion of an axial and lateral point-spread of light distribution pattern on said imaging plane.

* * * * *